United States Patent [19]

Boehringer et al.

[11] Patent Number: 5,354,262
[45] Date of Patent: Oct. 11, 1994

[54] APPARATUS FOR REMOVAL OF INSOLUBLE FAT FROM BLOOD OF A PATIENT

[75] Inventors: John R. Boehringer, Wynnewood; John Karpowicz, Glenmoore, both of Pa.

[73] Assignee: Boehringer Laboratories, Norristown, Pa.

[21] Appl. No.: 20,637

[22] Filed: Feb. 22, 1993

Related U.S. Application Data

[60] Division of Ser. No. 778,583, Oct. 17, 1991, Pat. No. 5,203,778, which is a continuation-in-part of Ser. No. 626,895, Dec. 13, 1990, which is a continuation-in-part of Ser. No. 406,820, Sep. 13, 1989, which is a continuation of Ser. No. 264,444, Oct. 28, 1988, abandoned, which is a continuation of Ser. No. 906,750, Sep. 12, 1986, Pat. No. 4,781,707, which is a continuation-in-part of Ser. No. 830,533, Feb. 18, 1986, Pat. No. 4,767,417.

[51] Int. Cl.$^5$ ............... A61M 37/00; A61M 1/00; A61M 1/14; A61M 1/34
[52] U.S. Cl. ............................. 604/4; 604/5; 604/317; 422/44
[58] Field of Search .................... 604/4–6, 604/49, 317; 422/44

[56] References Cited

U.S. PATENT DOCUMENTS 4,775,482 10/1988 Thurman .
5,203,778 4/1993 Boehringer et al. .................... 604/6

FOREIGN PATENT DOCUMENTS 0327136 8/1989 European Pat. Off. .
WO8602844 5/1986 PCT Int'l Appl. .

Primary Examiner—Randall L. Green
Assistant Examiner—P. Zuttarelli
Attorney, Agent, or Firm—Paul & Paul

[57] ABSTRACT

An apparatus is disclosed for treating blood, by having the blood enter a container, in which essentially insoluble fats (or lipids) are discriminately withdrawn out of the blood as the blood flows through or rises in the container, preferably by means of a wick that is in the container, as the level of blood in the container rises around the wick, such that essentially insoluble lipids on the upper surface of the rising blood are removed from the blood, leaving behind essentially aqueous components of the blood. Clots, bone chips and the like are also removed from the blood by means of a filter.

17 Claims, 1 Drawing Sheet

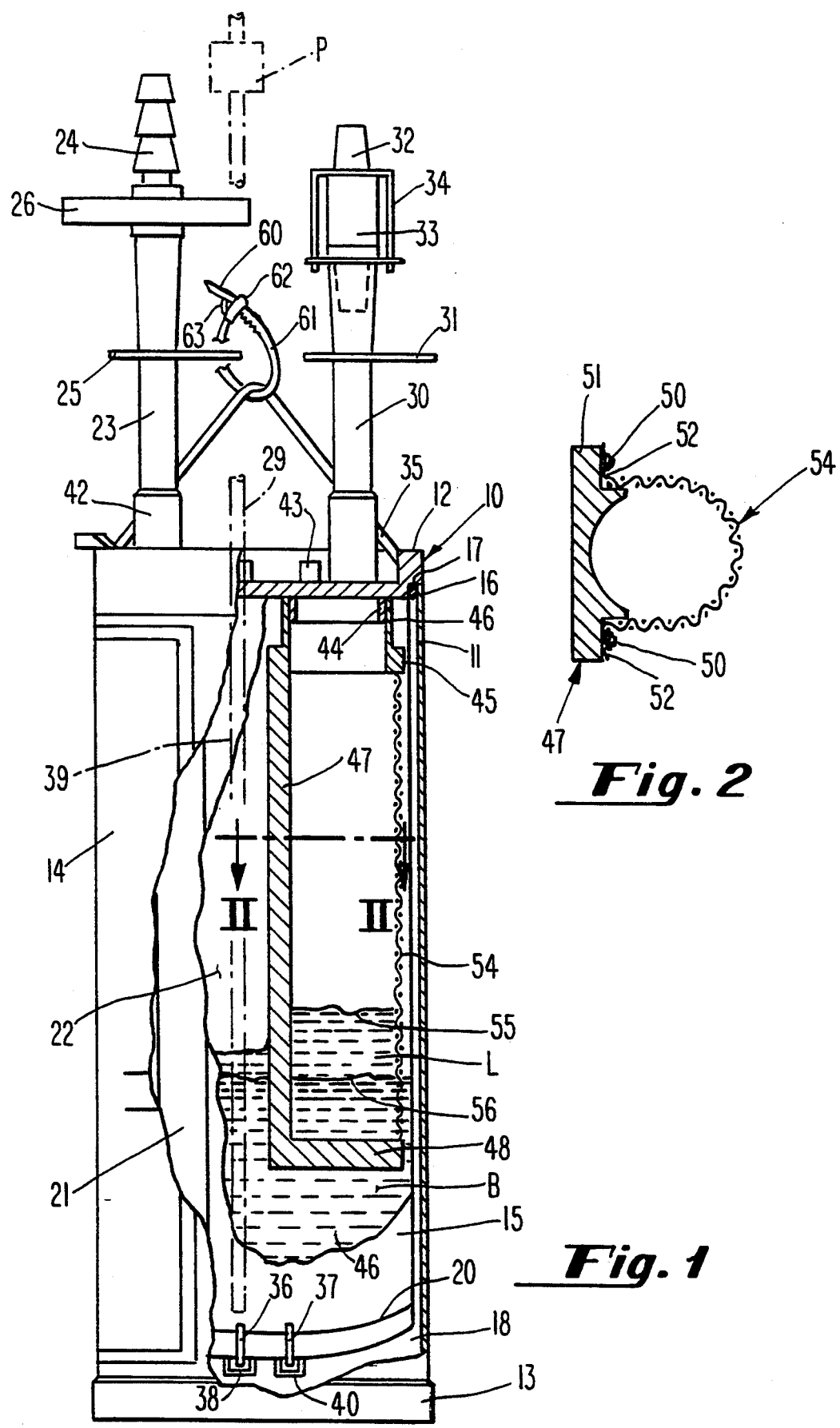

APPARATUS FOR REMOVAL OF INSOLUBLE FAT FROM BLOOD OF A PATIENT

CROSS-REFERENCE TO RELATED APPLICATIONS

This is a division of application Ser. No. 07/778,583, filed Oct. 17, 1991, now U.S. Pat. No. 5,203,778, which is a continuation-in-part of application Ser. No. 626,895 filed Dec. 13, 1990, which is continuation-in-part of application Ser. No. 406,820 filed Sep. 13, 1989, which is a continuation of application Ser. No. 264,444 filed Oct. 28, 1988, now abandoned, which is a continuation of application Ser. No. 906,750 filed Sep. 12, 1986; now U.S. Pat. No. 4,781,707, which is a continuation-in-part of application Ser. No. 830,533 filed Feb. 18, 1986; now U.S. Pat. No. 4,767,417.

BACKGROUND OF THE INVENTION

The present invention relates to a method for treating blood for the removal of insoluble fat therefrom, preferably for re-transfusion (autotransfusion) of the blood with the insoluble fat removed therefrom, back into the patient. This invention is directed to trauma, pre-operative, post-operative and intra-operative blood treatment.

Between intra-operative and post-operative blood re-use, post-operative blood collection for re-use has had increased medical interest, because the blood is generally freer of debris, contaminants and the like.

Re-use of blood has taken on increased interest with concern for possible contamination of a patient being transfused with blood other than the patient's own, during or after various types of surgery.

Accordingly, for example, during various operations of various kinds, be they emergency operations, chest, abdominal or limb operations, it is becoming increasingly commonplace to withdraw the blood from the patient, and to endeavor to collect that blood and return it reasonably promptly to the patient via intravenous techniques, generally after filtering clots or other debris, such as bone chips and the like therefrom, such as in accordance with the above-mentioned applications.

In accordance with the present invention, a number of observations have been made, and will be explained hereinafter, in connection with various orthopedic procedures, such as involve long bone fractures or other treatment procedures, hip replacements, knee replacement and the like, but it will be understood that fat removal in accordance with this invention may be desirable on the occasion of any type of surgery, trauma or any type of blood treatment. Consequently, references herein to orthopedic treatment and/or procedures will be considered to be by way of example only, and not limitations on the scope of the present invention.

One of the goals of the invention will therefore be the removal of free fats or lipids that are observed on the surface of blood collected post-operatively in orthopedic procedures, wherein it is intended that the blood be used for direct re-infusion. It is noted that such free lipids may occur floating on the top surface of blood collected in a container post-operatively, for example, following total joint arthroplasty. Such free lipids can be detected visually, appearing as a clear fluid floating on the top of the remainder of the liquid; namely the blood, sometimes having a clearly defined interface between the blood and the lipid. Sometimes this interface can be further distinguished by slightly agitating the collection reservoir, resulting in a disturbance of the free lipid such that it forms large globules surrounded by blood serum with the blood then settling to allow a clear, undisturbed layer to resurface. This clear layer is essentially the fats that are insoluble in blood.

The sources of insoluble liquid from procedures such as orthopedic procedures in the drainage fluid is the disturbed bone marrow and the surrounding adipose tissue. Such insoluble fats or lipids consist largely of mixed triglycerides.

The presence of the insoluble fats in the blood system, if allowed to be retransfused to the patient, can result in pulmonary fat embolisms in the lungs; occurrences in which fat globules constrict tiny passages in the lungs, limiting the breathing capacity of a patient, and sometimes resulting in death. The cause of the presence of such insoluble fat globules can be from the raining of fat from marrow into circulation as a result of trauma or excess pressure within the bone cavity, or from simply the presence of insoluble fats within the blood of a patient, by reasons of trauma from an accident, a medical procedure, or whatever reason.

Clinically, the syndrome of pulmonary fat embolism can present symptoms such as dyspnea, tachycardia, anxiety, confusion, focal neurologic deficits and coma. Such emboli may be revealed in chest x-rays, and may also be suggested by elevated body temperature.

Consequently, the pulmonary effects of orthopedic free lipid are a primary concern because this blood is administered via peripheral venous access.

In accordance with the present invention, significant amounts of free lipids (or insoluble fats) in the blood may be removed prior to re-transfusion of the blood. For example, it has been noted, in tests, that 93% of such insoluble fats have been removed (with the remainder coming into contact with and adhering to the walls of the vessel in which removal takes place). Thus, the wicking of such free lipids demonstrates the capability to remove large quantities of mixed triglyceride from the blood, to return the blood serum to near normal levels of triglycerides, which would be the soluble triglycerides.

SUMMARY OF THE INVENTION

In accordance with the present invention, essentially insoluble lipids or fats such as, but not limited to, generally mixed triglycerides, may be absorbed from the blood by wicking them out of the blood by contacting the blood with a wick that will allow insoluble fats to become distributed and accumulated in the wick while discriminating against the wicking of water or essentially aqueous components of blood into the wick. Such a wick will be a lipophilic and preferably also a hydrophobic material.

Accordingly, it is a primary object of this invention to provide a method for removing free, insoluble fats from blood while discriminating against the removal of the remainder of the blood, and to distribute and accumulate the free fats in the removal medium, preferably in blood that is to be used for re-transfusion to a patient, and preferably where the removal medium is a wicking means.

It is a further object of this invention to accomplish the above object, by wicking fats from the blood by the use of a hydrophobic lipophilic wick for absorbing insoluble fats from the blood.

Other objects of the invention are provided by any of the above objects, wherein a filter medium is provided for removing clots and/or bone chips or other debris from the blood.

It is another object of this invention to accomplish the above objects while the wick is protruding upwardly from an upper surface of the blood, and especially from an upper surface of a layer of insoluble fats carried on an upper surface of blood present in a container.

It is a further object of this invention to accomplish the above objects with respect to blood that is withdrawn from a patient for re-transfusion to a patient, and most especially for, but not limited to, orthopedic-related medical procedures.

Other objects and advantages of the present invention will be readily apparent upon a reading of the following brief descriptions of the drawing figures, the detailed descriptions of the preferred embodiments, and the appended claims.

BRIEF DESCRIPTION OF THE DRAWINGS

FIG. 1 is a front elevational view of a blood collection apparatus in accordance with one embodiment of the present invention, wherein the apparatus includes an outside cylindrical vessel, an inside bag-like vessel and a free fat wicking feature of the invention disposed inside the bag-like vessel, with portions of both the bag-like vessel and outer vessel being shown broken away, for clarity of illustration of the components inside the bag-like vessel, with the wicking feature components being shown in vertical section, for ease of illustration.

FIG. 2 is a transverse sectional view of the fat wicking and blood filtration components shown in FIG. 1, taken generally along lines II—II of FIG. 1.

DETAILED DESCRIPTION OF THE PREFERRED EMBODIMENTS

Referring now to the drawings in detail, reference is first made to FIG. 1, wherein there is illustrated an apparatus generally designated by the numeral 10, for collecting blood of a patient for re-use. The apparatus 10 includes a generally cylindrical, somewhat rigid plastic canister 11, having closed upper and lower ends 12 and 13, respectively. On the exterior of the canister or vessel 11, is a label 14, provided with suitable instructions, and the ability for having indicia written thereon, such as patient identification, blood type, and other medical information, etc. Carried by the top closure 12, and inside the outer vessel 11, is an inner vessel 15 of the bag type, the upper end of which, 16, is hermetically sealed by bonding to the lid 12 of the canister 11. The upper end of the canister 11 is likewise hermetically sealed to the lid 12 via o-ring 17. Such hermetic seals allow, during assembly of the apparatus 10, for drawing a reduced pressure on the zone 18 between the vessels 11 and to create a reduced pressure zone therebetween, prior to sealing closed the upper end of the vessel 11, to the container 12. Such hermetic seal allows the bag 15 to tend to hug the interior cylindrical surface of the vessel 11. The bag 15 is provided with a lower end 20.

On the exterior of the bag 20 is an indicia surface 21 in the form of a generally vertically disposed adhesive label strip or the like, to facilitate the nurse or other attendant writing the patient's name or other identifying indicia thereon, for proper identification at such time as the bag 15 is removed from the vessel 11, for re-use, as by re-transfusion to the patient.

Communicating with the interior zone 22 of the bag 15, is a vacuum draw conduit 23, connected to the zone 22 through the canister lid 12. The vacuum connection conduit 23 is provided with a connector 24, of generally conventional type, for connection to a source of lower pressure, such as to a partial vacuum pressure line normally available in hospital treatment rooms. One or more suitable shut-off clamps 25 are provided to clamp closed the flexible tubing 23, and thereby shut-off the drawing of vacuum from line 24 to the line 22, when it is not desired to draw a vacuum and draw blood from a patient into the zone 22.

A blood delivery line 30 is provided, also connected to communicate with the zone 22, through the lid 12. The line 30 is also of a flexible plastic tubing or the like, capable of being closed-off to prevent the passage of blood therethrough, by applying one or more shut-off clamps 31 thereto. Communicating with the blood flow line 30, is a line 32 for connection thereto at the upper end of the line 30, by means of a suitable fitting 33, with a band 34 holding the lower end of the tube 32 into the fitting to secure together the tubes or lines 32 and 30, for a sealing, non-leaking delivery line.

A hanger 35 is shown, carried by the upper closure 12, with the hanger being suitable to suspend the canister 11 from the conventional IV stand.

At the lower end 20 of the bag 15, there are provided conventional sealed spike ports 36 and 37, carried in their tabs 38 and 40, generally for invasion of the interior of the bag 15, for re-transfusion of the blood to the patient, after the bag 15 is removed from the canister 11, by insertion of a suitable needle or like conduit into one or more of the ports 36, 37, when autotransfusion is desirable.

In some applications, the container could have an open or partially open discharge end. For example, the discharge ports 36 and/or 37 could be opened to tubes through bottom 13 while the bag-container 15 is still receiving blood and the blood with free lipids removed could be delivered for reinfusion to the patient even while the container that contains the wicking means 47 or other free fat discriminating means is still being contacted by incoming blood. In such a situation, the bag-type container functions also somewhat as a conduit while functioning as a container. In other instances, the container could be more tube-like at the outset, with a wick or other free fat discriminator disposed in the tube-like container while the blood is flowing therethrough, all the while functioning like the wicking means 47 discussed herein. Thus the term "container" as used herein shall be sufficiently broad to encompass a conduit with one or more inlet and/or outlet openings.

As an alternative to using the discharge ports 36, 37 for delivering treated blood (i.e., with free lipids removed), to a patient, a dip tube 39, may optionally be used (shown in phantom in FIG. 1), reaching into the bottom of bag 15, through port 29, to remove the treated blood for delivering to a patient even while the blood treatment is on-going, with some means, such as a pump P being used to convey the blood to the patient.

At the upper end of the conduit 23, a hydrophobic filter 26 is provided, to facilitate drawing air through the line 23, when a vacuum is provided at 24, but for preventing the passage of blood through the fitting 42, in the event that the canister 11 should be upset or inverted for any reason. At the lower end of the conduit 23, a check valve (not shown) is provided to enable the device to maintain system vacuum when a temporary disconnect from a vacuum source is necessary. A sampling port 43 may be provided for periodically taking and testing of a sample of the blood, or for the addition of reagents, as desired.

The canister 11 and bag 15 and related portions of the apparatus 10 are constructed similar to corresponding components of U.S. Pat. No. 4,781,707, the complete disclosure of which is herein incorporated by reference herein.

Included within the container 12 is a blood entry duct 44, preferably cylindrical in shape. Around the duct 44 is a cylindrical mounting ring 45, which carries the wicking means and filter in the embodiment of this invention shown in FIGS. 1 and 2, being clampingly or friction-mounted to the duct 45, at 46. Depending from the mounting ring 45 is the wicking means 47 of the present invention, which extends into the bag 15, vertically downwardly, as shown in FIG. 1, in the form of a plate or the like (seen in FIG. 2). The wicking means 47 may terminate in a bottom wall 48, constructed of the same material as the rest of the wicking means 47 (which will be discussed hereinafter). The wicking means 47 may be constructed of a cross-sectional configuration as shown in FIG. 2, such that welds or seals 50 can secure outturned flanges 52 of filter 54 to a base 51 of wicking means 47. The filter 54 may be of a semi-rigid mesh-like construction, that, in the cross-section illustrated in FIG. 2 is of generally circular configuration.

However, by preferably constructing the wicking means 47 to be of rigid construction as shown, fats accumulated therein during blood treatment as described herein cannot accidently be squeezed out of the wicking means, by a nurse or other attendant, during reinfusion, and thus accidental reinfusion of the removed lipids to the patient is avoided. As an alternative, however, if release of fats from the wicking means is not a concern, the wicking means could be flexible and could be floating on the surface of the blood in its container.

As such, in the embodiment of FIGS. 1 and 2, the wicking means 47 and the filter 54, together, form an antechamber within the bag 15, that is closed in nature, such that all incoming blood passing through the duct 44 into the bag 15 will pass through the chamber. As the blood passes therethrough, it may travel along, but will not pass through the wicking means 47, but will pass out of the antechamber thus formed, by passing through the filter 54, The filter 54 will be of an appropriate mesh or pore size, such that it will filter blood clots, bone chips and the like from the blood, which pore size may be on the order of 170 microns, and will preferably be hydrophillic and lipophobic, so as to discourage ready passage of free lipids therethrough. The lipophobic nature of the filter will preferably allow a certain level of free lipids to be held back by the filter 54, at a level 55, for example. The relative lipophobic nature of the filter can be a function of its pore size, the relative pressure on the free lipids retained by the filter for the level 55 of such free lipids, and any surface treatment that would change the surface energy of the screen 54 to make it more capable of being "wet" by water-like substances like blood and less capable of being "wet" by fatty substances like lipids. Treatments are known that can affect surface energy of materials, in general. Such treatments might include flame treatments, radio frequency treatments, gas treatments and the like.

In order to facilitate emergency use, to hang the hanger 35 from any available device in the event that a suitable IV stand is not readily available, a flexible connector 60 is provided, having a bendable strip 61, adjustably connected through a catch mechanism 62, to hang the apparatus 10 from any available bed post, overhead support, or the like in emergency situations. The connector means will therefore be of the releasable type, having a release member 63, which when pulled open, of leftward as viewed in FIG. 1, will enable the end 60 to be withdrawn from connector member 62, to be re-applied after being disposed about a support structure.

With particular reference to FIG. 1, it will be seen that blood B will accumulate in the bottom of the bag 15, as the apparatus of this invention is being used, for example, to drain a wound. The upper surface of the liquid entering the bag 15, at 55, presents a layer of insoluble fats, or lipids "L" floating on the surface 56 of the remainder of the blood. As the liquid blood B accumulates in the bag 15, the upper surface 55 thereof, grows upwardly along the generally vertically disposed wicking means 47, such that the wicking means continues to present new surface portions to the accumulating level of blood, with the wicking means thus protruding upwardly and outwardly beyond the ever-increasing level of blood, with any lipids L carried on the upper surface thereof being contacted by the wicking means, and accumulated therein, by being distributed through the wicking means. The distribution of fats through the wicking means may or may not be uniform; that is, upon completing the use of a bag 15 of blood, it may be that the density of fats wicked therefrom is greater at the lower end of the wicking means than the upper end, but it will be apparent that Some distribution of fats or lipids will occur throughout the wicking means.

The wicking means 47 is adapted to remove essentially insoluble fat, such as triglycerides, cholesterol, fatty acids and lipo-proteins from blood that enters the interior of a bag in which it is disposed, upon the blood building up from the lower end of the bag, around the exterior of the wicking means 47. The wick is constructed of a hydrophobic lipophilic material, and it is comprised of polymeric material selected from a group such as a polyethylene, polypropylene, polystyrene, polyvinylchloride, polyvinylidene fluoride, polyester, ethylene-vinyl acetate, polytetra-fluoroethylene, stryene-acrylonitrile, tetrafluoroethylene and silicone, and most preferable it is comprised of the polymer polyethylene. The wick has a sufficient surface energy to allow a free liquid, fatty substance to be accumulated and spread therein, but will not allow more hydrophilic constituents of the blood, which are essentially the aqueous components of the blood, other than perhaps minor or trace amounts of such constituents of the blood, to be accumulated and spread therein.

Throughout this application, where the discrimination and/or removal of insoluble lipids is discussed it is to be understood that what is intended is essentially the removal of insoluble fats, leaving essentially the aqueous components of the blood behind. In this regard, it will be understood that perhaps not all of the insoluble lipids will be removed, with 100% certainty, but that a medically significant portion, and most often a clear major portion of the insoluble fats will be removed therefrom. Also, it will be understood that, along with removal of insoluble fats (or lipids), there will likely be removed other substances, while not being insoluble lipids per se, having an affinity for insoluble lipids and which will travel along therewith. Such other substances may include certain cholesterols that are soluble, the family of lipoproteins, phospholipids, clotting factors, trace elements of free hemoglobin, as well as small amounts of other components with affinity for free lipids, in that this list is not intended to all-encompassing. The principal components that are being discriminately removed from the essentially aqueous components of the blood, will, however, be the insoluble lipids; the other components or ingredients that are removed therewith will be those with affinity for the insoluble lipids, such that the discriminated and removed ingredients are thus defined as "essentially insoluble" fats (or lipids).

Similarly, what is left after removal of essentially the insoluble fats or lipids is essentially the aqueous components of the blood, which, while primarily including serum, albumin, saline and minerals, will also include those components of blood that have affinity for the aqueous components, which latter components can include, without intending to be a comprehensive listing, red and white blood cells, platelets, many antibodies and other components and ingredients with affinity for the aqueous components of blood. Such principally aqueous components of the blood and those other components of blood that have an affinity therefor are thus defined herein as "essentially aqueous components" of blood.

By wicking out the insoluble lipids in the blood, and leaving the soluble lipids behind, the present invention accomplishes a selective stripping or discrimination in the removed ingredients, that does not upset a balance in the blood by absorbing all or some soluble lipids indiscriminately, in that it leaves the soluble fats behind, which is important to the patient.

The pore size can be from 0-250 microns and more preferably it has been found that a wicking means which has pore sizes in the ranges of 10 to 100 microns is desirable for discriminately removing the free lipids while excluding the aqueous portion of the blood that would include the soluble lipids. Other structural characteristics of the wicking means may be that it is a solid, a foam, or other constructions that will accomplish the purposes of the present invention. Suck pore sizes can be arrived at by various techniques. For example only, if the wicking means is of rigid polyethylene construction, it can be made by polyethylene powder or grains, formed into the desired shape and then sintered to hold that shape by means of a hot gas. The actual pore sizes can be measured by any of various techniques, such as direct measurement, optical measurement, the imbibition method, the mercury injection method, the gas expansion method, density methods, or any other methods or techniques known in the measuring arts. See, for example, *Porous Media–Fluid Transport And Pore Structure* by F. A. L. Dullien, Academic Press, 1979.

In any event, the wicking means 47 will be imperforate to the passage of any but trace amounts of blood thereinto, at conventional transfusion pressures. Such pressures will normally be from atmospheric pressure at or near sea level, up to about 350 mm. mercury pressure.

It will thus be seen that the present invention readily lends itself to treating blood such that it can be re-infused into a patient, with the insoluble fats removed or substantially removed therefrom, as well as, with solid particles, bone chips and like also substantially removed therefrom, such that medical problems that might otherwise have been caused by the re-infusion of substantial quantities of insoluble fats or lipids might be avoided.

It will be apparent from the foregoing that various modifications may be made in the details of construction, as well as in the use and operation of the device of the present invention, within the spirit and scope of the invention as recited in the appended claims.

What is claimed is:

1. Apparatus for treating blood of a patient for reuse comprising:
   (a) a container for receiving blood from a body of the patient; and
   (b) including fat removal means disposed in the container, for removing essentially insoluble lipids from the blood; said fat removal means including a lipophilic discriminating means, that discriminates between essentially insoluble lipids in the blood and essentially aqueous components of the blood that includes soluble lipids, said fat removal means including means for accumulating essentially insoluble lipids separately from the essentially aqueous components of the blood that include soluble lipids by discriminating between said essentially soluble lipids and said essentially aqueous components of the blood that include soluble lipids.

2. The apparatus of claim 1, wherein said fat removal means is also a hydrophobic discriminating means.

3. The apparatus of claim 1, wherein said fat removal means includes means for distributing essentially insoluble lipids therein.

4. The apparatus of claim 1, wherein said fat removal means comprises a wicking means.

5. The apparatus of claim 4, wherein said lipophilic wicking means is comprised of a polymeric material selected from a group consisting of polyethylene, polypropylene, polystyrene, polyvinylchloride, polyvinylidene fluoride, polyester, ethylenevinyl acetate, polytetrafluoroethylene, styrene-acrylonitrile, tetrafluoroethylene and silicone.

6. The apparatus of claim 4, wherein said wicking means is comprised of the polymer polyethylene.

7. The apparatus of claim 4, wherein said wicking means is comprised of a polymeric material.

8. The apparatus of any one of claims 4–5, wherein said wicking means comprises a three-dimensional solid structure.

9. The apparatus of claim 8, wherein said solid structure has a cross-sectional construction of a pore size that makes it imperforate to passage of blood therethrough, at conventional transfusion pressures.

10. The apparatus of any one of claims 4–5, wherein a filter is provided as part of the apparatus, for intercepting blood delivered to the container; said filter being disposed such that all blood coming into the container passes therethrough; with the filter having perforation means for filtering blood clots, bone particles and the like therefrom, and having sufficient hydrophilic lipophobic characteristics as will retard the flow of essentially free lipids therethrough.

11. The apparatus of claim 10, wherein said wicking means and said filter define a closed antechamber in said container for blood received into said container; with said wicking means comprising at least one wall portion of said antechamber.

12. The apparatus of any one of claims 4–5, wherein said wicking means has a pore size of up to 250 microns, for facilitating the discrimination between essentially insoluble lipids in the blood and essentially aqueous components of the blood.

13. The apparatus of claim 12, wherein the pore size is within the range of 10–100 microns.

14. The apparatus of any one of claims 1–5, including dip tube means for withdrawing treated blood from the container.

15. Apparatus for treating blood of a patient for reuse comprising:
   (a) a container for receiving the blood from a body of the patient; and
   (b) including fat removal means disposed in the container for removing essentially insoluble lipids from the blood; said fat removal means including a lipophilic discriminating means, that discriminates between essentially insoluble lipids in the blood and essentially aqueous components of the blood that includes soluble lipids; said fat removal means including means for accumulating essentially insoluble lipids therein;
   (c) wherein said fat removal means comprises a wicking means; said wicking means comprising a generally vertical means adapted for disposition in the container, such that the increasing levels of blood in the container present an upper surface with essentially insoluble lipids carried thereon, which contacts increasingly higher portions of the wicking means projecting upwardly out of the upper blood surface, for removing the essentially insoluble lipids at the upper surface of the blood by contacting portions of the wicking means nearest the location of the protrusion of the wicking means out of the upper surface of the blood.

16. The apparatus of claim 15, wherein the container has an open inlet end and a closed discharge end for the essentially aqueous components of the blood.

17. The apparatus of claim 15, wherein said wicking means is constructed to be imperforate to passage of the essentially aqueous components of the blood therethrough at conventional transfusion pressures.

* * * * *

UNITED STATES PATENT AND TRADEMARK OFFICE
CERTIFICATE OF CORRECTION

PATENT NO. : 5,354,262
DATED : October 11, 1994
INVENTOR(S) : John R. Boehringer, et al.

It is certified that error appears in the above-indentified patent and that said Letters Patent is hereby corrected as shown below:

Col. 3, line 57, after "and" and before "to", -- 15, -- should be added.

Signed and Sealed this

Twenty-seventh Day of June, 1995

Attest:

BRUCE LEHMAN

Attesting Officer

Commissioner of Patents and Trademarks